(12) United States Patent
Zhao et al.

US007655660B2

(10) Patent No.: US 7,655,660 B2
(45) Date of Patent: Feb. 2, 2010

(54) PRODRUGS OF CC-1065 ANALOGS

(75) Inventors: Robert Yongxin Zhao, Watertown, MA (US); Ravi V. J. Chari, Newton, MA (US)

(73) Assignee: Immunogen Inc., Waltham, MA (US)

( * ) Notice: Subject to any disclaimer, the term of this patent is extended or adjusted under 35 U.S.C. 154(b) by 78 days.

(21) Appl. No.: 11/649,822

(22) Filed: Jan. 5, 2007

(65) Prior Publication Data

US 2007/0135346 A1 Jun. 14, 2007

Related U.S. Application Data

(62) Division of application No. 11/217,351, filed on Sep. 2, 2005, now Pat. No. 7,388,026, which is a division of application No. 10/692,856, filed on Oct. 27, 2003, now Pat. No. 7,049,316, which is a division of application No. 10/116,053, filed on Apr. 5, 2002, now Pat. No. 6,756,397.

(51) Int. Cl.
*A61K 31/497* (2006.01)
*C07D 241/04* (2006.01)

(52) U.S. Cl. .................... 514/252.2; 514/411; 514/318; 544/358; 548/414; 548/427

(58) Field of Classification Search ................. 514/411, 514/252.2, 318; 548/414, 427; 544/358
See application file for complete search history.

(56) References Cited

U.S. PATENT DOCUMENTS

| | | | |
|---|---|---|---|
| 5,475,092 | A | 12/1995 | Chari et al. |
| 5,585,499 | A | 12/1996 | Chari et al. |
| 5,843,937 | A | 12/1998 | Wang et al. |
| 5,846,545 | A | 12/1998 | Chari et al. |
| 6,060,608 | A | 5/2000 | Zhao |
| 6,534,660 | B1 | 3/2003 | Chari et al. |
| 6,548,530 | B1 | 4/2003 | Boger |
| 6,586,618 | B1 | 7/2003 | Zhao |
| 2003/0195365 | A1 | 10/2003 | Zhao |

FOREIGN PATENT DOCUMENTS

WO WO 03/087055 A1 10/2003

OTHER PUBLICATIONS

Chari et al., 1995, CAS: 123:306084.*
Katsushige Gomi, et al., "Anticellular and Antitumor Activity of Duocarmycins, Novel Antitumor Antibiotics," Jpn. J. Cancer Research, Jan. 1992, pp. 113-120, vol. 83.
Chong-Soon Lee, et al., "Determination of the Structural Features of (+) -CC-1065 That Are Responsible for Bending and Winding of DNA," Chem. Res. Toxicol., 1991, pp. 203-213, vol. 4, No. 2.
David H. Swenson, et al, "Evaluation of DNA Binding Characteristics of Some CC-1065 Analogs," Chem.-Biol. Interactions, 1988, pp. 199-213, vol. 67.
Li H. Li, et al., "Adozelesin, a selected lead among cyclopropylpyrroloindole analogs of the DNA-binding antibiotic, CC-1065," Investigational New Drugs, 1991, pp. 137-148, vol. 9, No. 2.
Bruce W. Ennis, et al., "The EGF Receptor System as a Target for Antitumor Therapy," Cancer Investigation, 1991, pp. 553-562, vol. 9, No. 5.
Magda C. Gutowski, et al., "Epidermal Growth Factor Receptor-reactive Monoclonal Antibodies: Xenograft Antitumor Activity Alone and as Drug Immunoconjugagtes," Cancer Res. 1991, pp. 5471-5475, vol. 51, No. 20.
Dale L. Boger, et al., "Parallel Synthesis and Evaluation of 132 (+)-1, 2, 9, 9aTetrahydrocyclopropa[c] benz [e] indol -4 -one (CBI Anaologues of CC-1065 and the Duocarmycins Defining the Contribution of the DNA-Binding Doman," Journal of Organic Chemistry, 2001, 66(20), 6654-6661. (abstract).
Yuqiang Wang, "Synthesis and Preliminary Biological Evaluations of CC-1065 Analogues: Effects of Different Linkers and Terminal Amides on Biological Activity," Journal of Medicinal Chemistry (2000), 43(8), 1541-1549.
International Search Report dated Feb. 8, 2007.
European Office Action issued Apr. 4, 2007, in EP03714044.9.
Dale L. Boger et al., "CBI Prodrug Analogs of CC-1065 and the Duocarmycins," Synthesis, no S.I., 1999, 1505-1509.
Alex Sparreboom et al., "Irinotecan (CPT-11) Metabolism and Disposition in Cancer Patients," Clinical Cancer Research, 1998, 4:2747-2754.
Scot Z. Fields et al., "Phase I Study of Etoposide Phosphate (Etopophos) as a 30-Minute Infusion on Days 1, 3, and 5," Clinical Cancer Research, 1995, 1:105-111.
Ravi V. J. Chari et al., "Enhancement of the Selectivity and Antitumor Efficacy of a CC-1065 Analogue through Immunoconjugate Formation," Cancer Research, 1995, 55: 4079-4084.

* cited by examiner

*Primary Examiner*—Rei-Tsang Shiao
(74) *Attorney, Agent, or Firm*—Sughrue Mion, PLLC

(57) ABSTRACT

Prodrugs of analogs of the anti-tumor antibiotic CC-1065 having a cleavable protective group such as a piperazino carbamate, a 4-piperidino-piperidino carbamate or a phosphate, in which the protecting group confers enhanced water solubility and stability upon the prodrug, and in which the prodrug also has a moiety, such as a disulfide, that can conjugate to a cell binding reagent such as an antibody. The therapeutic use of such prodrug conjugates is also described; such prodrugs of cytotoxic agents have therapeutic use because they can deliver cytotoxic prodrugs to a specific cell population for enzymatic conversion to cytoxic drugs in a targeted fashion.

7 Claims, 7 Drawing Sheets

FIGURE 1
FIG. 1A
PRIOR ART
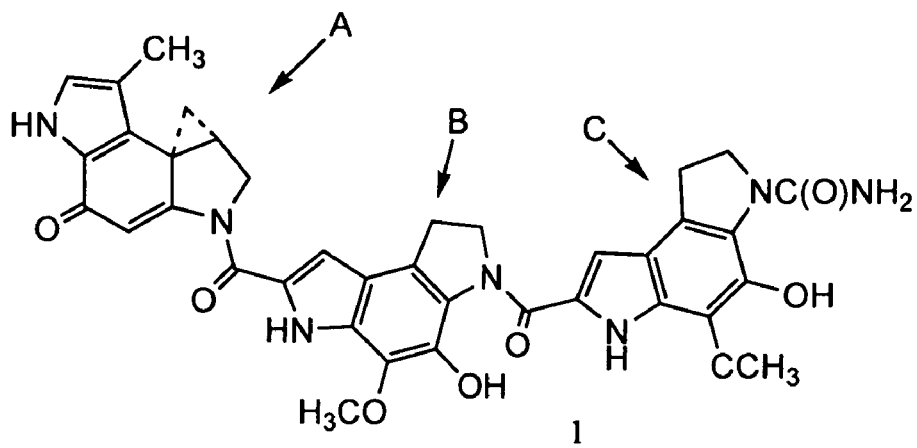
FIG. 1B
PRIOR ART
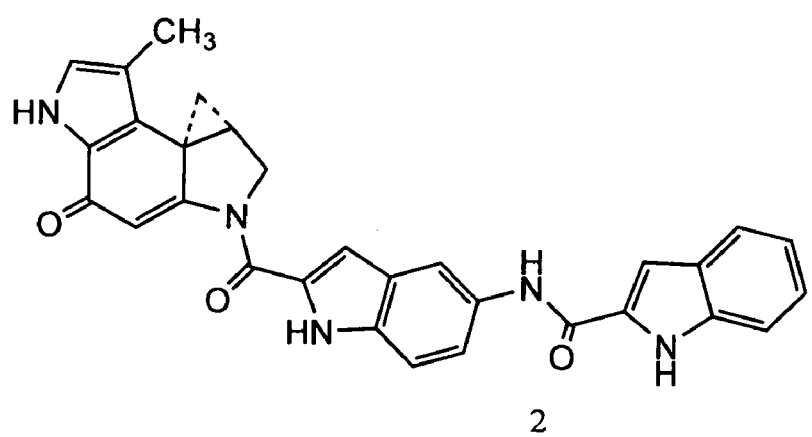
FIG. 1C
PRIOR ART
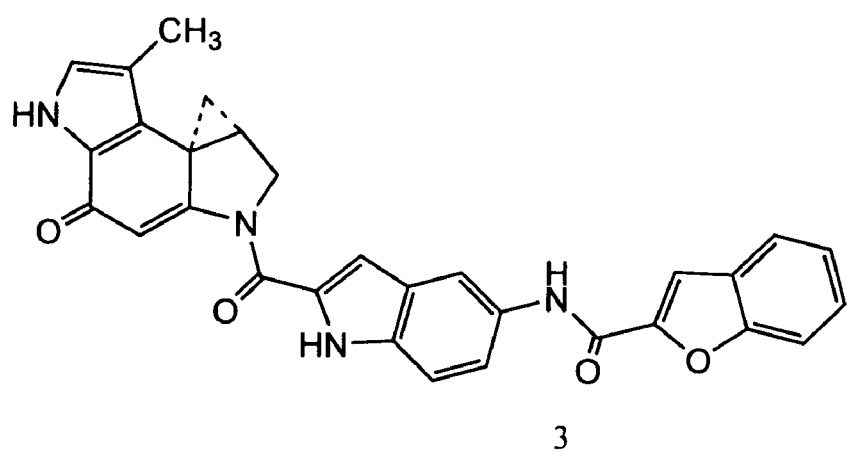

FIGURE 2
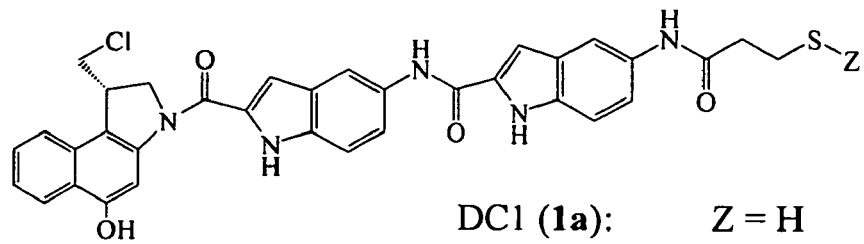
DC1 (1a): Z = H
DC1-SMe (1b): Z = SMe:
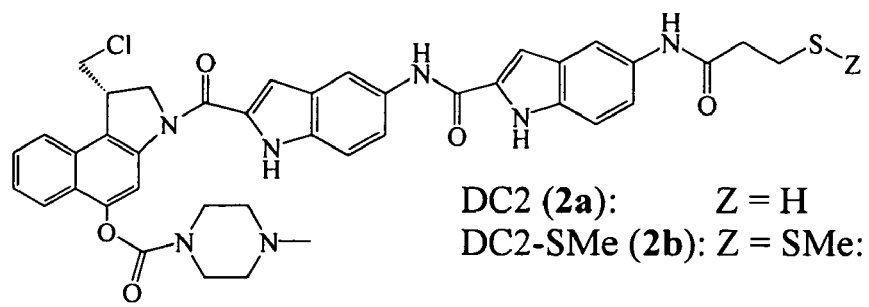
DC2 (2a): Z = H
DC2-SMe (2b): Z = SMe:
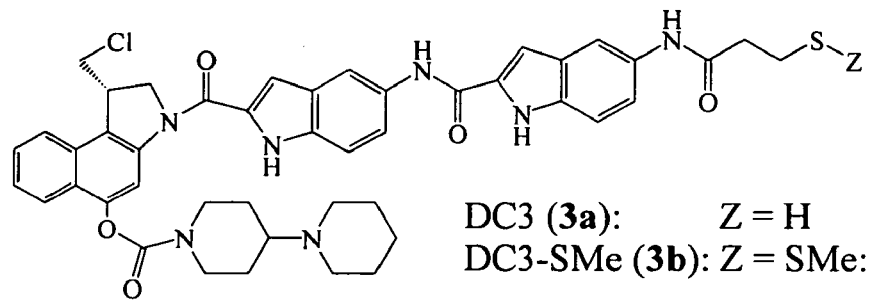
DC3 (3a): Z = H
DC3-SMe (3b): Z = SMe:
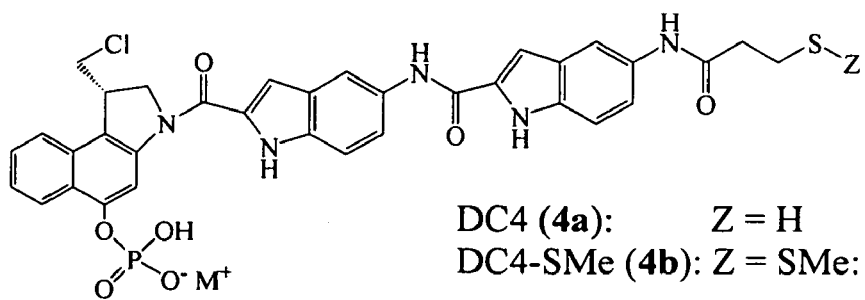
DC4 (4a): Z = H
DC4-SMe (4b): Z = SMe:
$M^+ = Na^+, K^+$ etc

FIGURE 3

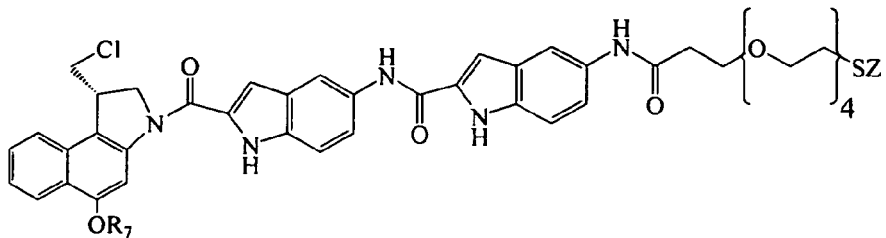

DC5 (5a)    Z = H       $R_7$ = H
DC5-SMe (5b) Z = SMe   $R_7$ = H

DC6 (6a)    Z = H       $R_7$ = ![piperazine-acetyl]

DC6-SMe (6b) Z = SMe    $R_7$ = ![piperazine-acetyl]

DC7 (7a)    Z = H       $R_7$ = ![piperidinyl-piperidine-acetyl]

DC7-SMe (7b) Z = SMe    $R_7$ = ![piperidinyl-piperidine-acetyl]

DC8 (8a)    Z = H       $R_7$ = $-\overset{\overset{\displaystyle OH}{\;}}{\underset{\underset{\displaystyle O}{\|}}{P}}-O^- M^+$ $M^+ = Na^+, K^+$ etc DC8-SMe (8b) Z = SMe    $R_7$ = $-\overset{\overset{\displaystyle OH}{\;}}{\underset{\underset{\displaystyle O}{\|}}{P}}-O^- M^+$

PRODRUGS OF CC-1065 ANALOGS

This is a divisional of application Ser. No. 11/217,351 filed Sep. 2, 2005 now U.S. Pat. No. 7,388,026, which is a divisional of application Ser. No. 10/692,856 filed Oct. 27, 2003 (now U.S. Pat. No. 7,049,316 which issued May 23, 2006), which is a divisional of application Ser. No. 10/116,053, filed Apr. 5, 2002 (now U.S. Pat. No. 6,756,397 which issued Jun. 29, 2004). The entire disclosures of said prior applications are hereby incorporated by reference.

FIELD OF THE INVENTION

The present invention relates to novel prodrugs of cytotoxic agents and their therapeutic uses. More specifically, the invention relates to novel prodrugs of cytotoxic agents that are analogs of CC-1065 and which comprise both a moiety for chemical linkage to a cell binding agent and a protecting group that is cleaved in vivo. The prodrugs can be chemically linked to cell binding agents to provide therapeutic agents capable of being activated and released in vivo, and delivered to specific cell populations in a targeted manner.

BACKGROUND OF THE INVENTION

Many reports have appeared which are directed to the targeting of tumor cells with monoclonal antibody-drug conjugates {Sela et al, in Immunoconjugates, pp. 189-216 (C. Vogel, ed. 1987); Ghose et al, in Targeted Drugs, pp. 1-22 (E. Goldberg, ed. 1983); Diener et al, in Antibody Mediated Delivery Systems, pp. 1-23 (J. Rodwell, ed. 1988); Pietersz et al, in Antibody Mediated Delivery Systems, pp. 25-53 (J. Rodwell, ed. 1988); Bumol et al, in Antibody Mediated Delivery Systems, pp. 55-79 (J. Rodwell, ed. 1988); G. A. Pietersz & K. Krauer, 2 J. Drug Targeting, 183-215 (1994); R. V. J. Chari, 31 Adv. Drug Delivery Revs., 89-104 (1998); W. A. Blattler & R. V. J. Chari, in Anticancer Agents, Frontiers in Cancer Chemotherapy, 317-338, ACS Symposium Series 796; and I. Ojima et al eds, American Chemical Society 2001}. Cytotoxic drugs such as methotrexate, daunorubicin, doxorubicin, vincristine, vinblastine, melphalan, mitomycin C, chlorambucil, calicheamicin and maytansinoids have been conjugated to a variety of murine monoclonal antibodies. In some cases, the drug molecules were linked to the antibody molecules through an intermediary carrier molecule such as serum albumin {Garnett et al, 46 Cancer Res. 2407-2412 (1986); Ohkawa et al, 23 Cancer Immunol. Immunother. 81-86 (1986); Endo et al, 47 Cancer Res. 1076-1080 (1980)}, dextran {Hurwitz et al, 2 Appl. Biochem. 25-35 (1980); Manabi et al, 34 Biochem. Pharmacol. 289-291 (1985); Dillman et al, 46 Cancer Res. 4886-4891 (1986); and Shoval et al, 85 Proc. Natl. Acad. Sci. U.S.A. 8276-8280 (1988)}, or polyglutamic acid {Tsukada et al, 73 J. Natl. Canc. Inst. 721-729 (1984); Kato et al, 27 J. Med. Chem. 1602-1607 (1984); Tsukada et al, 52 Br. J. Cancer 111-116 (1985)}.

A wide array of linkers is now available for the preparation of such immunoconjugates, including both cleavable and non-cleavable linkers. In vitro cytotoxicity tests, however, have revealed that antibody-drug conjugates rarely achieve the same cytotoxic potency as the free unconjugated drugs. This has suggested that mechanisms by which drug molecules are released from conjugated antibodies are very inefficient. Early work in the area of immunotoxins showed that conjugates formed via disulfide bridges between monoclonal antibodies and catalytically active protein toxins were more cytotoxic than conjugates containing other linkers {Lambert et al, 260 J. Biol. Chem. 12035-12041 (1985); Lambert et al, in Immunotoxins 175-209 (A. Frankel, ed. 1988); Ghetie et al, 48 Cancer Res. 2610-2617 (1988)}. This improved cytotoxicity was attributed to the high intracellular concentration of reduced glutathione contributing to the efficient cleavage of the disulfide bond between the antibody molecule and the toxin. Maytansinoids and calicheamicin were the first examples of highly cytotoxic drugs that had been linked to monoclonal antibodies via disulfide bonds. Antibody conjugates of these drugs have been shown to possess high potency in vitro and exceptional antitumor activity in human tumor xenograft models in mice {R. V. J. Chari et al., 52 Cancer Res., 127-131 (1992); C. Liu et al., 93, Proc. Natl. Acad. Sci., 8618-8623 (1996); L. M. Hinman et al., 53, Cancer Res., 3536-3542 (1993); and P. R. Hamann et al, 13, BioConjugate Chem., 40-46 (2002)}.

An attractive candidate for the preparation of such cytotoxic conjugates is CC-1065, which is a potent anti-tumor antibiotic isolated from the culture broth of *Streptomyces zelensis*. CC-1065 is about 1000-fold more potent in vitro than are commonly used anti-cancer drugs, such as doxorubicin, methotrexate and vincristine {B. K. Bhuyan et al., Cancer Res., 42, 3532-3537 (1982)}.

The structure of CC-1065 (Compound 1, FIG. 1A) has been determined by x-ray crystallography {Martin, D. G. et al, 33 J. Antibiotics 902-903 (1980), and Chidester, C. G., et al, 103 J. Am. Chem. Soc. 7629-7635 (1981)}. The CC-1065 molecule consists of 3 substituted pyrroloindole moieties linked by amide bonds. The "A" subunit has a cyclopropyl ring containing the only asymmetric carbons in the molecule. While only the relative configuration of these carbons is available from x-ray data, the absolute configuration has been inferred as 3b-R, 4a-S, by using DNA as a chiral reagent {Hurley, L. H. et al, 226 Science 843-844 (1984)}. The "B" and "C" subunits of CC-1065 are identical pyrroloindole moieties.

The cytotoxic potency of CC-1065 has been correlated with its alkylating activity and its DNA-binding or DNA-intercalating activity. These two activities reside in separate parts of the molecule. Thus, the alkylating activity is contained in the cyclopropapyrroloindole (CPI) subunit and the DNA-binding activity resides in the two pyrroloindole subunits (FIG. 1A).

However, although CC-1065 has certain attractive features as a cytotoxic agent, it has limitations in therapeutic use. Administration of CC-1065 to mice caused a delayed hepatotoxicity leading to mortality on day 50 after a single intravenous dose of 12.5 μg/kg {V. L. Reynolds et al., J. Antibiotics, XXIX, 319-334 (1986)}. This has spurred efforts to develop analogs that do not cause delayed toxicity, and the synthesis of simpler analogs modeled on CC-1065 has been described {M. A. Warpehoski et al., J. Med. Chem., 31, 590-603 (1988)}. In another series of analogs, the CPI moiety was replaced by a cyclopropabenzindole (CBI) moiety {D. L. Boger et al., J. Org. Chem., 55, 5823-5833, (1990), D. L. Boger et al., BioOrg. Med. Chem. Lett., 1, 115-120 (1991)}. These compounds maintain the high in vitro potency of the parental drug, without causing delayed toxicity in mice. Like CC-1065, these compounds are alkylating agents that bind to the minor groove of DNA in a covalent manner to cause cell death. However, clinical evaluation of the most promising analogs, Adozelesin and Carzelesin, has led to disappointing results {B. F. Foster et al., Investigational New Drugs, 13, 321-326 (1996); I. Wolff et al., Clin. Cancer Res., 2,1717-1723 (1996)}. These drugs display poor therapeutic effects because of their high systemic toxicity.

The therapeutic efficacy of CC-1065 analogs can be greatly improved by changing the in vivo distribution through targeted delivery to the tumor site, resulting in lower toxicity to non-targeted tissues, and thus, lower systemic toxicity. In order to achieve this goal, conjugates of analogs and derivatives of CC-1065 with cell-binding agents that specifically target tumor cells have been described {U.S. Pat. Nos.; 5,475, 092; 5,585,499; 5,846,545} all of which are incorporated herein by reference in their entirety. These conjugates typically display high target-specific cytotoxicity in vitro, and exceptional anti-tumor activity in human tumor xenograft models in mice {R. V. J. Chari et al., *Cancer Res.*, 55, 4079-4084 (1995)}.

Cell-binding agents are typically only soluble in aqueous medium, and are usually stored in aqueous solutions. Thus, these analogs should possess sufficient water solubility to allow for efficient reaction with cell-binding agents and subsequent formulation in aqueous solution. In addition, for cell-binding agent conjugates to have a useful shelf life, it is important that CC-1065 analogs that are linked to these cell-binding agents are stable for an extended period of time in aqueous solutions.

The CC-1065 analogs described thus far (see, e.g. FIGS. 1B and 1C) are only sparingly soluble in water. Because of the sparing solubility of CC-1065 analogs, conjugation reactions with cell-binding agents currently have to be performed in extremely dilute aqueous solutions. Therefore, these prodrugs should have enhanced water solubility as compared to the parent drugs.

Also, CC-1065 analogs that have been described thus far are quite unstable in aqueous solutions for the following reason. The seco-form of the drug is spontaneously converted into the cyclopropyl form, which then may alkylate DNA, if present. However, the competing reaction of the cyclopropyl form with water results in opening of the cyclopropyl ring to yield the hydroxy compound, which is inactive. Thus, there is a need to protect the reactive portion of CC-1065 analogs in order to extend their useful life in aqueous solution, for example by the development of prodrugs of CC-1065 analogs.

There is therefore a need to develop prodrugs of CC-1065 analogs that are very stable upon storage in aqueous solutions. Preferably, these prodrugs should only be converted into active drugs in vivo. Once the prodrug is infused into a patient, it should preferably be efficiently converted into active drug.

Carzelesin is a prodrug where the phenolic group in adozelesin is protected as a phenyl carbamate {L. H. Li et al., *Cancer Res.*, 52, 4904-4913 (1992)}. However, this prodrug is too labile for therapeutic use, and also affords no increase in water solubility compared to the parental drug. In a second example, the phenolic residue of a CC-1065 analog was glycosylated to produce a prodrug (U.S. Pat. No. 5,646,298). However, this prodrug is not converted into active drug in vivo, and requires the additional administration of an enzyme from a bacterial source to convert it to the cytotoxic form.

There are a few examples of anticancer drugs, unrelated to CC-1065, that have been converted into water soluble prodrugs. In the anticancer drug irinotecan, the phenolic group is protected by a 4-piperidino-piperidino carbamate. It has been reported that this protecting group confers water solubility to the drug. In addition, the prodrug is readily converted in vivo in humans to the active drug, presumably by the enzyme carboxylesterase, which naturally exists in human serum, tumor tissue and in some organs {A. Sparreboom, 4, *Clin. Cancer Res.*, 2747-2754 (1998). L. P. Rivory et al., 52, *Biochem Pharmacol.*, 1103-1111 (1996)}.

Similarly, the anticancer drug etoposide phosphate is an example of a prodrug that has a phosphate protecting group and is rapidly converted into active drug in vivo, presumably through hydrolysis by endogenous alkaline phosphatase {S. Z. Fields et al., 1 *Clin. Cancer Res.*, 105-111 (1995)}.

Thus, there exists a need for analogs of CC-1065 that have increased solubility and stability in aqueous solution, to facilitate their conjugation to cell binding agents in aqueous solutions, while preserving their biological activity. In addition, in order to reduce toxic side-effects, it would be advantageous to provide the CC-1065 analog in the form of a prodrug that is converted to the cytotoxic drug predominantly at the desired therapeutic site and preferably through the action of endogenous agents. All these advantages and more are provided by the invention described herein, as will be apparent to one of skill in the art upon reading the following disclosure and examples.

SUMMARY OF THE INVENTION

The object of the present invention is to provide prodrugs of CC-1065 analogs, which have enhanced stability and solubility in aqueous medium. This and other objects have been achieved by providing prodrugs in which the phenolic group of the alkylating portion of the molecule is protected with a functionality that renders the drug stable upon storage in aqueous solution. In addition, the protecting group confers increased water solubility to the drug compared to an unprotected analog. The protecting group is readily cleaved in vivo to give the corresponding active drug. In the prodrugs described herein, the phenolic substituent is preferentially protected as a piperazino carbamate, a 4-piperidino-piperidino carbamate or as a phosphate, each of which possesses a charge at physiological pH, and thus have enhanced water solubility. In order to further enhance water solubility, an optional polyethylene glycol spacer has been introduced into the linking group between the terminal indolyl subunit C and the cleavable linkage such as a disulfide group. The introduction of this spacer does not alter the potency of the drug.

A more specific embodiment of the invention provides a prodrug that comprises an analog of a seco-cyclopropabenzindole-containing cytotoxic drug that has a protecting group, which enhances water solubility and stability and that can be cleaved in vivo. The prodrug of this specific embodiment has a first and a second subunit that are linked by an amide bond from the secondary amino group of the pyrrole moiety of the first subunit to the C-2 carboxyl of the second subunit. The first subunit is shown as formula (I), and is conjugated to the second subunit, which is selected from among formulae (II)-(IX):

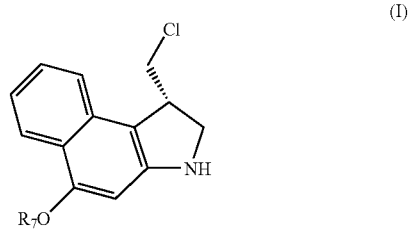

-continued

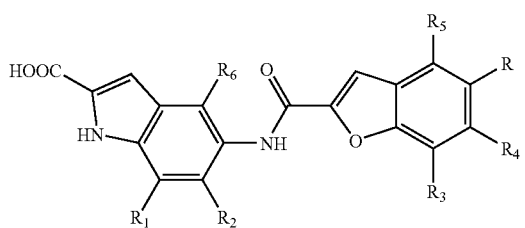

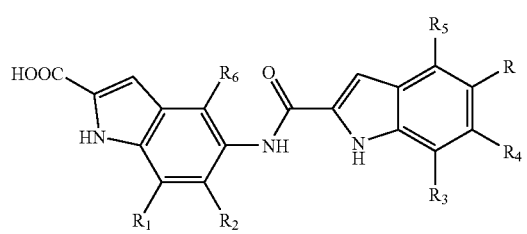

in which R represents a linking group that provides for linkage of the prodrug to a cell binding agent, where such linkage is preferably via a disulfide bond. The linking group may comprise a polyethylene glycol spacer. $R_1$-$R_6$ are each independently hydrogen, $C_1$-$C_3$ linear alkyl, methoxy, hydroxyl, primary amino, secondary amino, tertiary amino, or amido. $R_7$ is the protecting group that can be cleaved in vivo and enhances water solubility of the cyclopropabenzindole-containing cytotoxic drug, and is preferably a piperazino carbamate, a 4-piperidino-piperidino carbamate or a phosphate.

The prodrugs of the invention can be used in cytotoxic conjugates in which a cell binding agent is linked to one or more of the prodrugs of the present invention. Cell binding agents include antibodies and fragments thereof, interferons, lymphokines, vitamins, hormones and growth factors. Pharmaceutical compositions containing such conjugates are also provided.

The cytotoxic conjugates can be used in a method for treating a subject by administering an effective amount of the above pharmaceutical composition. According to the cell-type to which the selected cell binding agent binds, many diseases may be treated either in vivo, ex vivo or in vitro. Such diseases include, for example, the treatment of many kinds of cancers, including lymphomas, leukemias, cancer of the lung, breast, colon, prostate, kidney, pancreas, and the like.

Thus, there are provided prodrugs of CC-1065 analogs that have improved solubility and stability in aqueous solution, and which retain cytotoxicity when activated to produce an alkylating drug, and which are useful in the targeting of specific cell types by means of conjugation to a specific cell binding agent.

BRIEF DESCRIPTION OF THE FIGURES

FIG. 1A shows the structure of CC-1065 and its subunits A, B, and C.

FIG. 1B and FIG. 1C show the structures of two known analogs of CC-1065.

FIG. 2 shows the structures of exemplary CC-1065 analogs and prodrugs of the present invention.

FIG. 3 shows the structures of exemplary polyethylene glycol-containing prodrugs of the present invention.

DETAILED DESCRIPTION OF THE INVENTION

Figure 4A:
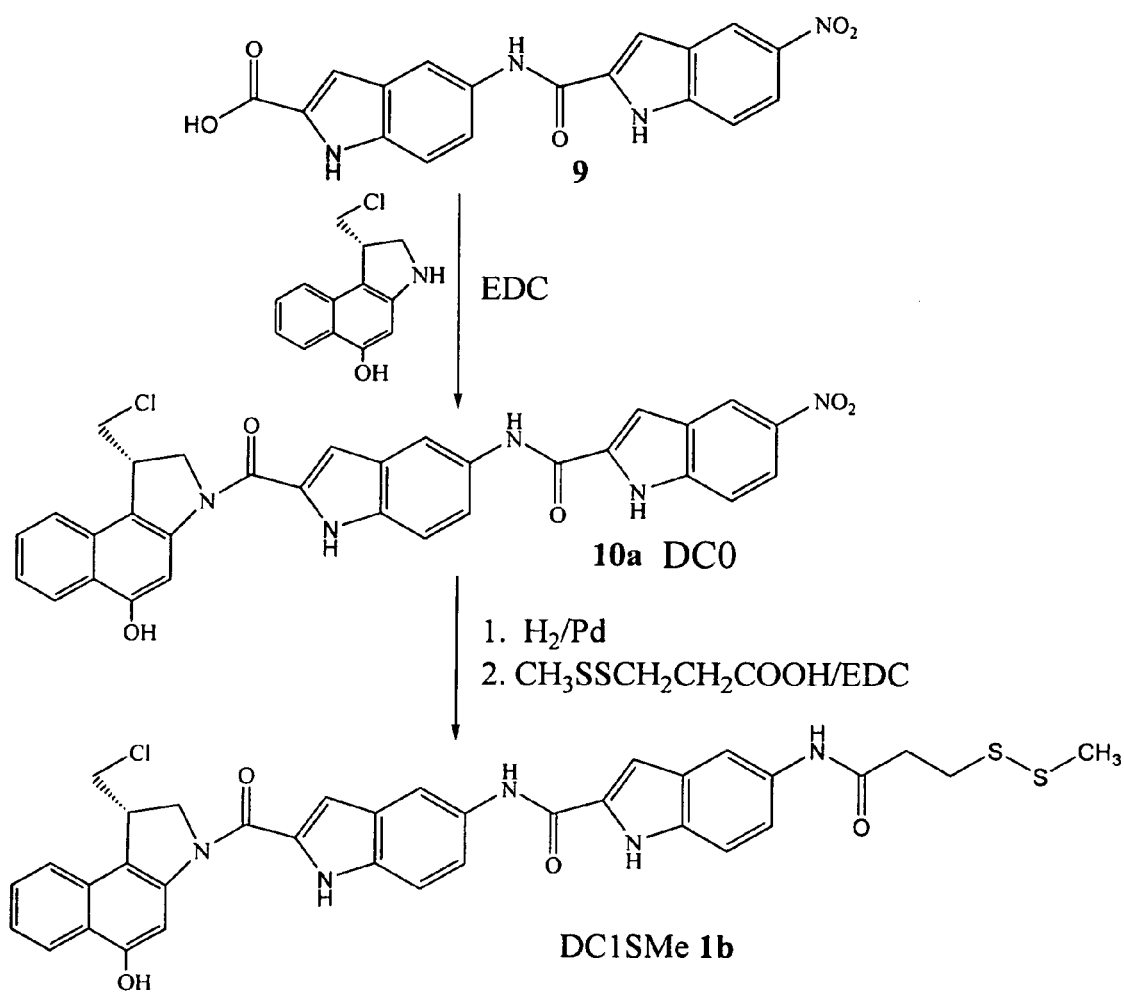
FIGS. 4A and B are synthesis schemes for preparing (S)-N-[2-{(1-chloromethyl)-1,2-dihydro-5-[(4-methylpiperazino)carbonyloxy]-3H-benz(e)indol-3-yl}carbonyl]-1H-indol-5-yl]-5-[(3-mercapto-1-oxopropyl)-amino]-1H-indole-2-carboxamide (DC2) and (S)-N-[2-{(1-chloromethyl)-1,2-dihydro-5-[(4-piperidino-piperidino)carbonyloxy]-3H-benz(e)indol-3-yl}carbonyl]-1H-indol-5-yl]-5-[(3-mercapto-1-oxopropyl)-amino]-1H-indole-2-carboxamide (DC3).

The present inventors have found that the stability, water solubility and utility of certain CC-1065 analogs are enhanced by protection of the alkylating moiety of the analog with a suitable protecting group. The inventors have thereby provided prodrugs of CC-1065 analogs having enhanced aqueous solubility and stability and which are further capable of linkage to cell binding agents whereby the therapeutic efficacy of such prodrugs of CC-1065 analogs is improved by changing the in vivo distribution through targeted delivery of the prodrug to the tumor site, resulting in a lower toxicity to non-targeted tissues, and hence lower systemic toxicity. Upon delivery of the prodrug, endogenous substances substantially convert the prodrug to its active drug form, and, in embodiments having a cleavable linker to the cell binding agent, the active drug form of the CC-1065 analog is released, thus further enhancing its cytotoxic activity. Alternatively, the linker to the cell binding agent may be first cleaved inside the target cell to release the prodrug, followed by endogenous conversion into the active drug.

In order to achieve this goal, the inventors synthesized exemplary prodrugs (FIGS. 2-6) of CC-1065 analogs that are seco-cyclopropabenzindole (CBI)-containing cytotoxic prodrugs comprising: (a) a first subunit of formula (I) that is protected at the phenolic hydroxyl by a protecting group to enhance stability and water solubility and which is cleaved in vivo, and (b) a second subunit having the structure represented by one of formulae (II)-(IX) and which comprises a linking group for conjugation of the prodrug to a cell binding agent. The linking group can contain a polyethylene glycol spacer (FIG. 3). Removal of the protecting group of the prodrug produces an active form of the drug that retains the high cytotoxicity of the parent drug. The linker is used for conjugation to cell binding agents, preferably via a disulfide bond.

It has previously been shown that the linkage of highly cytotoxic drugs to antibodies using a cleavable link, such as a disulfide bond, ensures the release of fully active drug inside the cell, and that such conjugates are cytotoxic in an antigen specific manner {R. V. J. Chari et al, 52 Cancer Res. 127-131 (1992); R. V. J. Chari et al., 55 Cancer Res. 4079-4084 (1995); and U.S. Pat. Nos. 5,208,020 and 5,475,092}. In the present invention, the inventors describe the synthesis of prodrugs of CC-1065 analogs, procedures for their conjugation to monoclonal antibodies and for measurement of the in vitro cytotoxicity and specificity of such conjugates. Thus the invention provides useful compounds for the preparation of therapeutic agents directed to the elimination of diseased or abnormal cells that are to be killed or lysed such as tumor cells, virus infected cells, microorganism infected cells, parasite infected cells, autoimmune cells (cells that produce auto-antibodies), activated cells (those involved in graft rejection or graft vs. host disease), or any other type of diseased or abnormal cells, while exhibiting minimal side effects.

Thus, this invention teaches the synthesis of prodrug analogs and derivatives of CC-1065 that can be chemically linked to a cell binding agent and that maintain, upon release of the protective group, the high cytotoxicity of the parent compound CC-1065. Further, upon activation, these compounds when linked to a cell binding agent are cytotoxic to cells to which the cell binding agent binds and are much less toxic to non-target cells.

Prodrugs of the Present Invention

The prodrugs according to the present invention comprise an analog of CC-1065 in which the phenolic group of the alkylating portion of the molecule is protected and the prodrug further comprises a linker capable of conjugating the prodrug to a cell binding agent. The prodrug may comprise a first and a second subunit that are linked via an amide bond.

According to certain embodiments of the present invention, the prodrug of the CC-1065 analog has a first subunit that is a seco-CBI (cyclopropabenzindole unit) in its open chloromethyl form, wherein the first subunit has a phenolic hydroxyl that is protected by a water-soluble protecting group that can be cleaved in vivo. The second subunit of the prodrug of certain embodiments of the present invention comprises an analog of the combined B and C subunits of CC-1065 (FIG. 1) that are 2-carboxy-indole or 2-carboxy-benzofuran derivatives, or both, and are represented by formulae (II)-(IX). As may be ascertained from the natural CC-1065 and from the properties of the analogs that have been published {e.g. Warpehoski et al, 31 J. Med. Chem. 590-603 (1988), Boger et al, 66 J. Org. Chem. 6654-6661 (2001)}, the B and C subunits can also carry different substituents at different positions on the indole or benzofuran rings, corresponding to positions $R_1$-$R_6$ of formulae (II)-(IX), and still retain potent cytotoxic activity.

In order to link the prodrug of the CC-1065 analog to a cell-binding agent, the prodrug must first include a moiety that allows the derivatives to be linked to a cell binding agent via a cleavable linkage such as a disulfide bond, an acid-labile group, a photo-labile group, a peptidase-labile group, or an esterase-labile group. The prodrug analogs are prepared so that they contain a moiety necessary to link the analog to a cell binding agent via, for example, a disulfide bond, an acid-labile group, a photo-labile group, a peptidase-labile group, or an esterase-labile group. In order to further enhance solubility in aqueous solutions, the linking group can contain a polyethylene glycol spacer (FIG. 3).

Preferably, a disulfide linkage is used because the reducing environment of the targeted cell results in cleavage of the disulfide and release of the prodrug (or drug, depending on the relative sequence of cleavage of the prodrug from the cell binding agent and hydrolysis of the protecting group), with an associated increase in cytotoxicity.

More specifically, according to certain embodiments of the present invention, the prodrug of an analog of CC-1065 comprises first and second subunits that are covalently linked via an amide bond from the secondary amino group of the pyrrole moiety of the first subunit to the C-2 carboxy group of the second subunit having the formulae (II)-(IX).

Within formulae (II)-(IX), R represents a moiety that enables linkage of the prodrug of a CC-1065 analog to a cell binding agent. The linking moiety may contain a polyethylene glycol spacer. Examples include moieties that enable linkages via disulfide bond, an acid-labile group, a photolabile group, a peptidase-labile group, or an esterase-labile group, and are well-known in the art {see, e.g., U.S. Pat. No. 5,846,545, which is incorporated herein by reference}. Preferred moieties are those that enable linkage via a disulfide bond, for example a thiol (DC1, DC2, DC3, DC4, DC5, DC6, DC7) or a disulfide (DC1-SMe, DC2-SMe, DC3-SMe, DC4-SMe, DC5-SMe, DC6-SMe, DC7-Sme, see FIGS. 2-6). Mixed disulfides containing any terminal leaving group, such as thiomethyl (DC1-SMe, DC2-SMe, DC3-SMe, DC4-SMe, DC5-SMe, DC6-SMe, DC7-SMe), glutathione, alkyl thiol, thiopyridyl, aryl thiol, and the like may be used provided that such disulfides are capable of undergoing a disulfide-exchange reaction for the coupling of the prodrug to a cell binding agent. R can optionally further comprise a spacer region interposed between the reactive group of the linkage-enabling portion and the 2-carboxy-indole or 2-carboxy-benzofuran derivative portion. Preferred embodiments include $NHCO(CH_2)_mSZ$, $NHCOC_6H_4(CH_2)_mSZ$, or $O(CH_2)_mSZ$, $NHCO(CH_2)_m(OCH_2CH_2)_nSZ$, $NHCOC_6H_4(CH_2)_m(OCH_2CH_2)_nSZ$, or $O(CH_2)_m(OCH_2CH_2)_nSZ$ wherein: Z represents H or $SR_8$, wherein $R_8$ represents methyl, linear alkyl, branched alkyl, cyclic alkyl, simple or substituted aryl or heterocyclic, and m represents an integer of 1 to 10, n represents an integer of 4 to 1000. Examples of linear alkyls represented by $R_8$ include methyl, ethyl, propyl, butyl, pentyl and hexyl. Examples of branched alkyls represented by $R_8$ include isopropyl, isobutyl, sec.-butyl, tert.-butyl, isopentyl and 1-ethyl-propyl. Examples of cyclic alkyls represented by $R_8$ include cyclopropyl, cyclobutyl, cyclopentyl and cyclohexyl. Examples of simple aryls represented by $R_8$ include phenyl and naphthyl. Examples of substituted aryls represented by $R_8$ include aryls such as phenyl or naphthyl substituted with alkyl groups, with halogens, such as Cl, Br, F, nitro groups, amino groups, sulfonic acid groups, carboxylic acid groups, hydroxy groups and alkoxy groups. Heterocyclics represented by $R_8$ are compounds wherein the heteroatoms are selected from O, N, and S, and examples include furyl, pyrrollyl, pyridyl, (e.g., a 2-substituted pyrimidine group) and thiophene. Most preferred embodiments of R include $NHCO(CH_2)_2SH$ and $NHCO(CH_2)_2SSCH_3$. $NHCO(CH_2)_2(OCH_2CH_2)_nSH$ and $NHCO(CH_2)_2(OCH_2CH_2)_nSSCH_3$.

Within formulae (II)-(IX), $R_1$ to $R_6$, which may be the same or different, independently represent hydrogen, $C_1$-$C_3$ linear alkyl, methoxy, hydroxyl, primary amino, secondary amino, tertiary amino, or amido. Examples of primary amino group-containing substituents are methyl amino, ethyl amino, and isopropyl amino. Examples of secondary amino group-containing substituents are dimethyl amino, diethyl amino, and ethyl-propyl amino. Examples of tertiary amino group-containing substituents are trimethyl amino, triethyl amino, and ethyl-isopropyl-methyl amino. Examples of amido groups include N-methyl-acetamido, N-methyl-propionamido, N-acetamido, and N-propionamido.

Within formulae (II)-(IX), $R_7$ is an in vivo-cleavable protecting group that enhances water solubility of the seco-cyclopropabenzindole-containing cytotoxic drug. Examples of preferred in vivo-cleavable protecting groups are piperazino carbamate, a 4-piperidino-piperidino carbamate and a phosphate, and derivatives thereof. Thus, piperazino carbamate and 4-piperidino-piperidino carbamate protecting groups are enzyme-cleavable by enzymes such as carboxyl esterase, which occurs in serum and plasma. Phosphate protecting groups are cleavable by phosphatase enzymes such as alkaline phosphatase.

Disulfide-containing and mercapto-containing prodrugs of CC-1065 analogs of the present invention can be evaluated for their ability to suppress proliferation of various unwanted cell lines in vitro only after they have been activated. For example, phosphoryl group-containing prodrugs, such as DC4, can be activated by incubation with commercially available alkaline phosphatases, while carbamate-containing prodrugs, such as DC3 and DC4, can be activated by incubation with commercially available carboxyl esterases. Cell lines such as, for example, the human epidermoid carcinoma line KB, the human breast tumor line SK-BR-3, and the Burkitt's lymphoma line Namalwa can easily be used for the assessment of the cytotoxicity of these compounds. Cells to be evaluated can be exposed to the compounds for 24 hours and the surviving fractions of cells measured in direct assays by known methods. $IC_{50}$ values can then be calculated from the results of the assays.

Preparation of Cell Binding Agents

The effectiveness of the prodrug compounds of the invention as therapeutic agents depends upon the careful selection of an appropriate cell binding agent. Cell binding agents may be of any kind presently known, or that become known, and include peptides and non-peptides. Generally, these can be antibodies (especially monoclonal antibodies) or a fragment of an antibody that contains at least one binding site, lymphokines, hormones, growth factors, nutrient-transport molecules (such as transferrin), or any other cell binding molecule or substance. More specific examples of cell binding agents that can be used include:

monoclonal antibodies;

single chain antibodies;

fragments of antibodies such as Fab, Fab', $F(ab')_2$ and $F_v$, {Parham, 131 J. Immunol. 2895-2902 (1983); Spring et al, 113 J. Immunol. 470-478 (1974); Nisonoff et al, 89 Arch. Biochem. Biophys. 230-244 (1960)};

interferons;

peptides;

lymphokines such as IL-2, IL-3, IL-4, IL-6;

hormones such as insulin, TRH (thyrotropin releasing hormones), MSH (melanocyte-stimulating hormone), steroid hormones, such as androgens and estrogens;

growth factors and colony-stimulating factors such as EGF, TGFα, insulin like growth factor (IGF-I, IGF-II) G-CSF, M-CSF and GM-CSF {Burgess, 5 Immunology Today 155-158 (1984)}; vitamins, such as folate and transferrin {O'Keefe et al, 260 J. Biol. Chem. 932-937 (1985)}.

Monoclonal antibody technology permits the production of extremely selective cell binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins.

Selection of the appropriate cell binding agent is a matter of choice that depends upon the particular cell population that is to be targeted, but in general monoclonal antibodies are preferred if an appropriate one is available.

For example, the monoclonal antibody MY9 is a murine $IgG_1$, antibody that binds specifically to the CD33 Antigen {J. D. Griffin et al 8 Leukemia Res., 521 (1984)} and can be used if the target cells express CD33 as in the disease of acute myelogenous leukemia (AML). Similarly, the monoclonal antibody anti-B4 is a murine $IgG_1$, that binds to the CD19 antigen on B cells {Nadler et al, 131 J. Immunol. 244-250 (1983)} and can be used if the target cells are B cells or diseased cells that express this antigen such as in non-Hodgkin's lymphoma or chronic lymphoblastic leukemia.

Additionally, GM-CSF which binds to myeloid cells can be used as a cell binding agent to diseased cells from acute myelogenous leukemia. IL-2, which binds to activated T-cells, can be used for prevention of transplant graft rejection, for therapy and prevention of graft-versus-host disease, and for the treatment of acute T-cell leukemia. MSH, which binds to melanocytes, can be used for the treatment of melanoma.

Preparation of Prodrug Conjugates

Conjugates of the prodrugs and a cell binding agent can be formed using any techniques presently known or later developed. An indolyl, benzofuranyl, bis-indolyl, bis-benzofuranyl, indolyl-benzofuranyl, or benzofuranyl-indolyl derivative coupled to the seco-CBI analog can be prepared to contain a free amino group and then linked to an antibody or other cell binding agent via an acid labile linker, or by a photolabile linker. The prodrug compounds can be condensed with a peptide having a suitable sequence and subsequently linked to a cell binding agent to produce a peptidase labile linker. Cytotoxic compounds can be prepared to contain a primary hydroxyl group, which can be succinylated and linked to a cell binding agent to produce a conjugate that can be cleaved by intracellular esterases to liberate free prodrug. Preferably, the prodrug compounds are synthesized to contain a free or protected thiol group, with or without a PEG-containing spacer, and then one or more disulfide or thiol-containing prodrugs are each covalently linked to the cell binding agent via a disulfide bond.

Representative conjugates of the invention are conjugates of prodrugs of CC-1065 analogs with antibodies, antibody fragments, epidermal growth factor (EGF), melanocyte stimulating hormone (MSH), thyroid stimulating hormone (TSH), estrogen, estrogen analogs, androgen, and androgen analogs.

Representative examples of the preparation of various conjugates of prodrugs of CC-1065 analogs and cell binding agents are described below.

Disulfide linkers: Antibody N901 which binds to the CD-56 antigen that is expressed on the surface of small cell lung cancer cells {J. D. Griffin, T. Hercend, R. Beveridge & S. F. Schlossman, J. Immunol, 130:2947 (1983)} can be used for the preparation of conjugates. The antibody is modified with N-succinimidyl-3-pyridyldithio propionate as previously described {J. Carlsson, H. Drevin & R. Axen, Biochem. J., 173:723 (1978)} to introduce, on the average, 4 pyridyldithio groups per antibody molecule. The modified antibody is reacted with the thiol-containing prodrug to produce a disulfide-linked conjugate.

Acid-Labile Linkers: Amino group-containing prodrugs of the present invention can be linked to antibodies and other cell binding agents via an acid labile linker as previously described. {W. A. Blattler et al, Biochemistry 24, 1517-1524 (1985); U.S. Pat. Nos. 4,542,225, 4,569,789, 4,618,492, 4,764,368}.

Similarly, an hydrazido group-containing prodrug of the present invention can be linked to the carbohydrate portion of antibodies and other cell binding agents via an acid labile hydrazone linker {for examples of hydrazone linkers see B. C. Laguzza et al, J. Med. Chem., 32, 548-555 (1989); R. S. Greenfield et al, Cancer Res., 50, 6600-6607 (1990)}.

Photo-Labile Linkers: Amine group containing prodrugs of the present invention may be linked to antibodies and other cell binding agents via a photolabile linker as previously described {P. Senter et al, Photochemistry and Photobiology, 42, 231-237 (1985); U.S. Pat. No. 4,625,014}.

Peptidase-Labile Linkers: Amine group containing prodrugs of the present invention may also be linked to cell binding agents via peptide spacers. It has been previously shown that short peptide spacers between drugs and macromolecular protein carriers are stable in serum but are readily hydrolyzed by intracellular peptidases {A. Trouet et al, Proc. Natl. Acad. Sci., 79, 626-629 (1982)}. The amino group containing containing prodrugs may be condensed with peptides using condensing agents such as 1-ethyl-3-(3-dimethylaminopropyl)carbodiimide-HCl (EDC-HCl) to give a peptide derivative that can be linked to cell binding agents.

Esterase-Labile Linkers: Prodrugs of the present invention bearing a hydroxy alkyl group may be succinylated with succinic anhydride and then linked to a cell binding agent to produce a conjugate that can be cleaved by intracellular esterases to liberate free drug. {For examples see E. Aboud-Pirak et al, Biochem Pharmacol., 38, 641-648 (1989)}.

The conjugates made by the above methods can be purified by standard column chromatography or by HPLC.

Preferably conjugates between monoclonal antibodies or cell binding agents and prodrugs of the present invention are those that are joined via a disulfide bond, as discussed above. Such cell binding conjugates are prepared by known methods such as modifying monoclonal antibodies with succinimidyl pyridyl-dithiopropionate (SPDP) {Carlsson et al, 173 Biochem. J. 723-737 (1978)}. The resulting thiopyridyl group is then displaced by treatment with thiol containing prodrug to produce disulfide linked conjugates. Conjugates containing 1 to 10 prodrugs linked via a disulfide bridge are readily prepared by this method. Conjugation by this method is fully described in U.S. Pat. No. 5,585,499, which is incorporated by reference.

In Vitro Cytotoxicity of Conjugates between Cell Binding Agents and Prodrugs of the Present Invention Cytotoxicity of the prodrugs of the present invention and their conjugates with cell binding agents can be measured after cleavage of the protecting group and conversion into the active drug. Cytotoxicity to non-adherent cell lines such as Namalwa and SW2 can be measured by back-extrapolation of cell proliferation curves as described in Goldmacher et al, 135 J. Immunol. 3648-3651 (1985). Cytotoxicity of these compounds to adherent cell lines such as A-375 and SCaBER can be determined by clonogenic assays as described in Goldmacher et al, 102 J. Cell Biol. 1312-1319 (1986).

Therapeutic Agent and Method for Inhibiting the Growth of Selected Cell Populations The present invention also provides a therapeutic agent for inhibiting the growth of selected cell populations comprising:

(a) a cytotoxic amount of one or more of the above-described prodrugs linked to a cell binding agent, and (b) a pharmaceutically acceptable carrier, diluent or excipient.

Similarly, the present invention provides a method for inhibiting the growth of selected cell populations comprising contacting a cell population or tissue suspected of containing cells from said selected cell population with a cytotoxic amount of a cytotoxic agent comprising one or more of the above-described prodrugs linked to a cell binding agent.

The cytotoxic agent is prepared as described above.

Suitable pharmaceutically acceptable carriers, diluents, and excipients are well known and can be determined by those of skill in the art as the clinical situation warrants.

Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

The method for inhibiting the growth of selected cell populations can be practiced in vitro, in vivo, or ex vivo.

Examples of in vitro uses include treatments of cell cultures in order to kill all cells except for desired variants that do not express the target antigen; or to kill variants that express undesired antigen.

The conditions of non-clinical in vitro use are readily determined by the skilled artisan.

Examples of ex vivo uses include treatments of autologous bone marrow prior to their transplant into the same patient in order to kill diseased or malignant cells: treatments of bone marrow prior to their transplantation in order to kill competent T cells and prevent graft-versus-host-disease (GVHD).

Clinical ex vivo treatment to remove tumor cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent GVHD, can be carried out as follows. Bone marrow is harvested from the patient or other individual and then incubated in medium containing serum to which is added the cytotoxic agent of the invention, concentrations range from about 10 μM to 1 pM, for about 30 minutes to about 48 hours at about 37° C. The exact conditions of concentration and time of incubation (=dose) are readily determined by the skilled artisan. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as solutions that are tested for sterility and for endotoxin levels or as a lyophilized solid that can be redisolved in sterile water for injection. Examples of suitable protocols of conjugate administration are as follows. Conjugates are given weekly for 6 weeks as an i.v. bolus. Bolus doses are given in 50 to 400 ml of normal saline to which human serum albumin (e.g. 0.5 to 1 mL of a concentrated solution of human serum albumin, 100 mg/mL) can be added. Dosages will be about 50 μg to 10 mg/kg of body weight per week, i.v. (range of 10 μg to 100 mg/kg per injection). Six weeks after treatment, the patient may receive a second course of treatment. Specific clinical protocols with regard to route of administration, excipients, diluents, dosages, times, etc., can be determined by the skilled artisan as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, and lymphatic organs; melanomas; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; bacterial infection; and parasite infections, such as giardiasis, amoebiasis, schistosomiasis, and others as determined by one skilled in the art.

EXAMPLES

The invention will now be illustrated by reference to non-limiting examples. Unless otherwise stated, all percents, ratios, parts, etc. are by weight.

Materials and Methods

Melting points were measured using an Electrothermal apparatus and are uncorrected. NMR spectra were recorded on a Bruker AVANCE400 (400 MHz) spectrometer. Chemical shifts are reported in ppm relative to TMS as an internal standard. Mass spectra were obtained using a Bruker Esquire 3000 system. Ultraviolet spectra were recorded on a Hitachi U1200 spectrophotometer. HPLC was performed using a Beckman Coulter GOLD 125 system equipped with a Beckman Coulter system GOLD 168 variable wavelength detector and a Waters RADIALPAK, (a reverse phase C-18 column). Thin layer chromatography was performed on Analtech GF silica gel TLC plates. Silica gel for flash column chromatography was from Baker. Tetrahydrofuran was dried by distillation over sodium metal. Dimethylactamide and dimethylformamide were dried by distillation over calcium hydride under reduced pressure. All other solvents used were reagent grade or HPLC grade.

The synthesis of prodrugs DC2 (2), DC3 (3) and DC4 (4) DC5 DC6 DC7 DC8 (FIGS. 2-6) is described herein. DC2, DC3 and DC4 are derived from the parent drug DC1, while DC6, DC7 and DC8 can be prepared from the pegylated parent drug DC5. The prodrugs DC2 and DC3 are extremely stable in aqueous solutions, and can be converted into the parent drug DC1 by incubation in serum, plasma or with an enzyme such as carboxyl esterase. These drugs also have enhanced water solubility as compared with DC1. The prodrug DC4 is also extremely stable in aqueous solutions and also soluble. Incubation of DC4 with alkaline phosphatase converts it into the parent drug DC1.

Figure 4B:
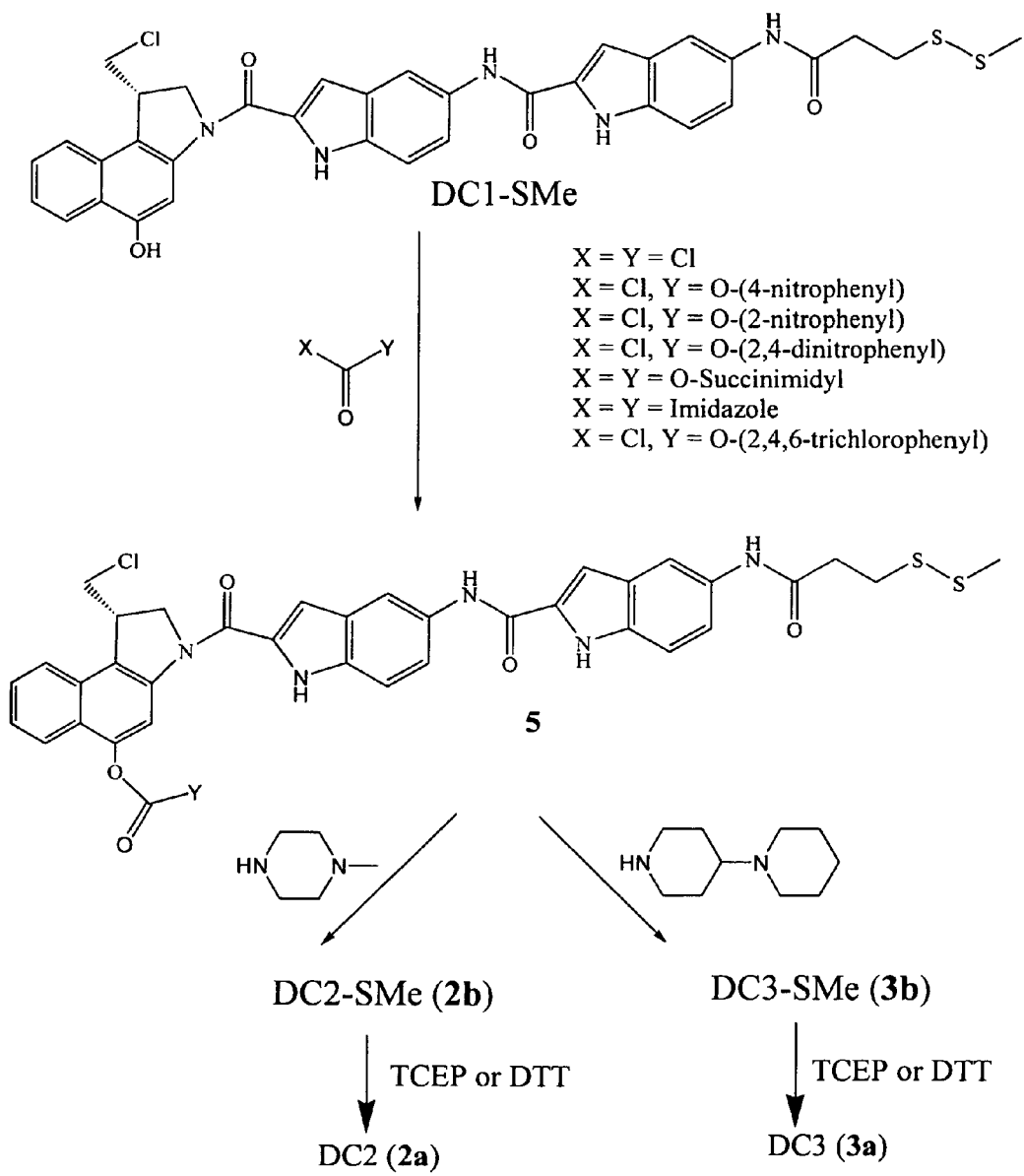
Figure 5:
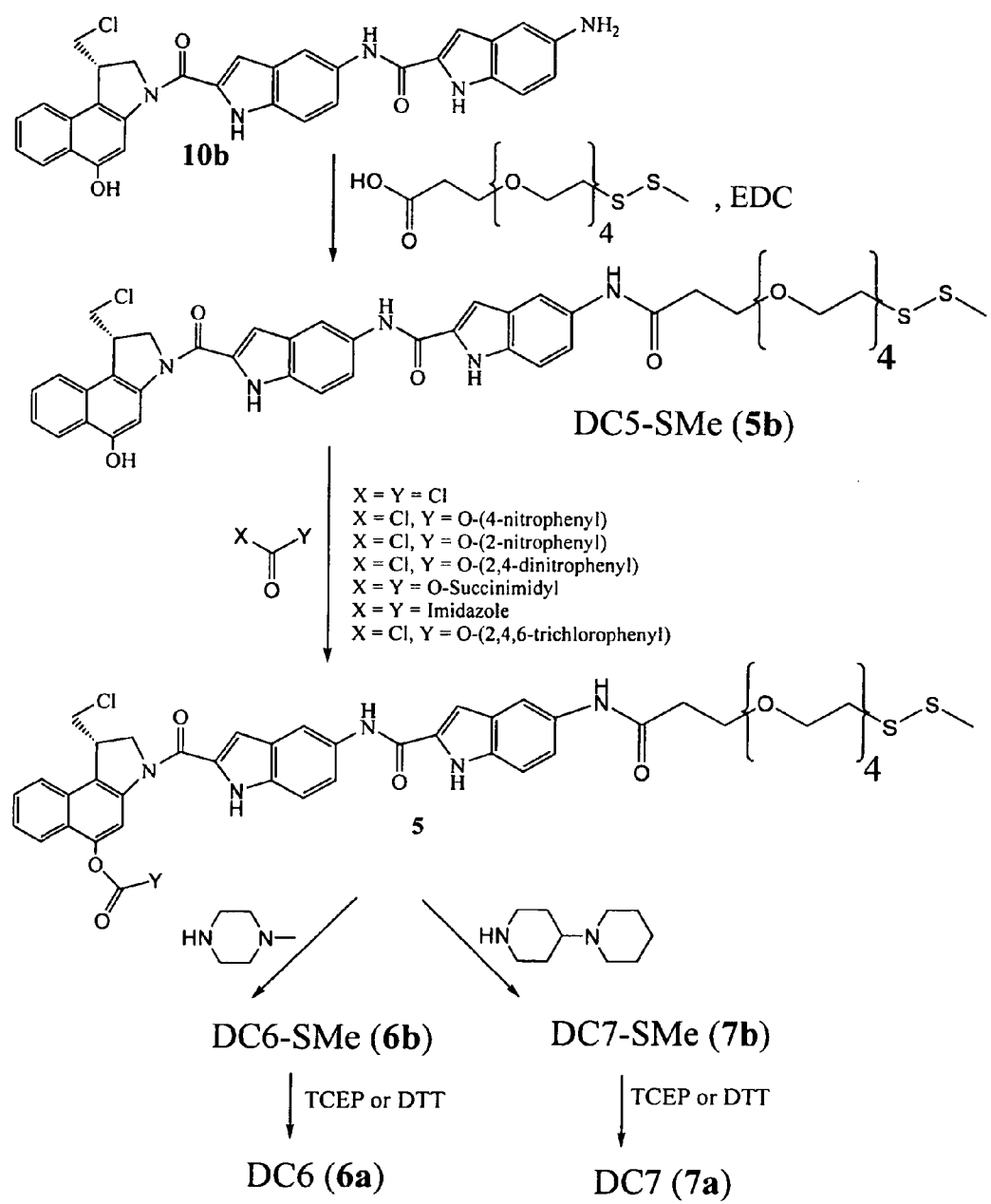
FIG. 5 shows schemes for the synthesis of PEGylated versions of DC1, DC2 and DC3, which are DC5, DC6 and DC7, respectively.

The synthetic scheme for the conversion of DC1 (1) to the prodrugs DC2 (2) and DC3 (3) is shown in FIG. 4. The phenolic substituent on DC1 can be reacted with any one of the reagents listed in FIG. 3 to give the intermediate 5. Reaction of 5 with N-methylpiperazine provides DC2. Reaction of 5 with 4-piperidino-piperidine provides DC3.

Figure 6:
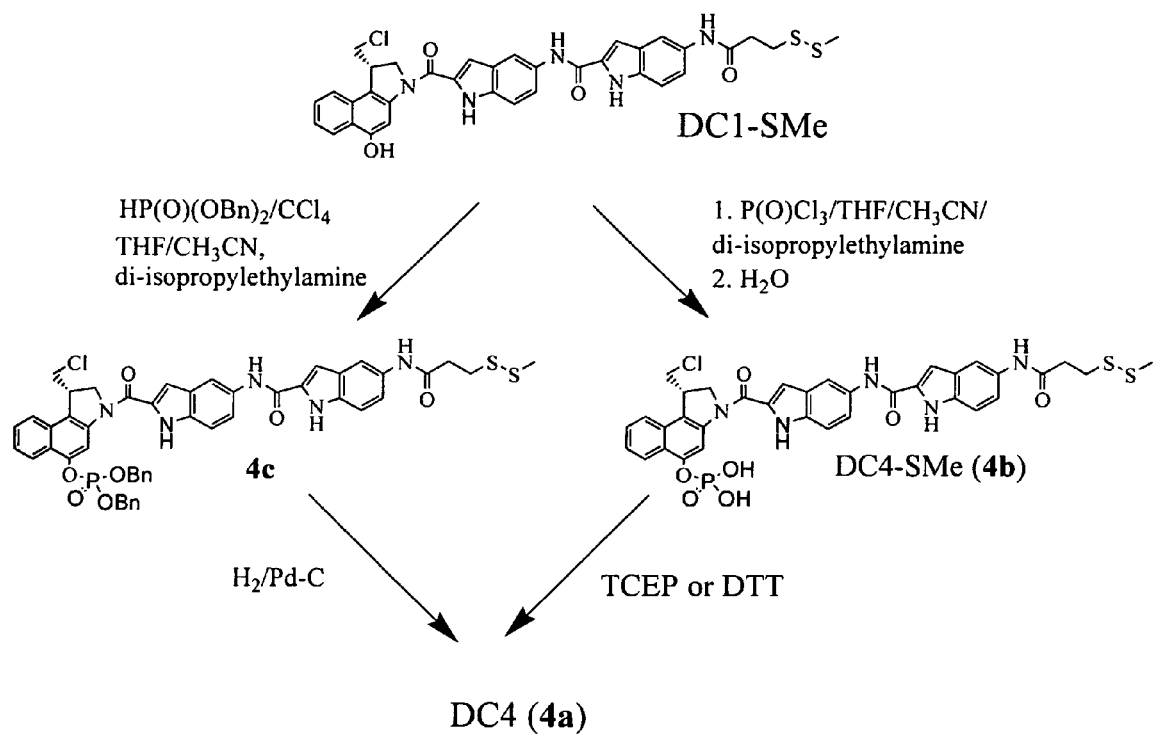
FIG. 6 shows two synthetic schemes for the preparation of (S)-N-[2-{(1-chloromethyl)-1,2-dihydro-5-(phosphonoxy)-3H-benz(e)indol-3-yl}carbonyl]-1H-indol-5-yl]-5-[(3-mercapto-1-oxopropyl)-amino]-1H-indole-2-carboxamide (DC4)).

DC1 was converted to the prodrug DC4 as shown in FIG. 6. Treatment of DC1-SMe with dibenzylphosphate and carbon tetrachloride in the presence of base provided the intermediate 4c, while reaction of DC1-SMe with phosphorous oxychloride provide intermediate 4b. Removal of the benzyl protecting groups of 4c with hydrogen, with concomitant reduction of the disulfide bond provided DC4. Reduction of intermediate 4b with TCEP or DTT provided DC4.

Example I

Preparation of (S)-N-[2-{(1-chloromethyl)-1,2-dihydro-5-[(4-methylpiperazino)carbonyloxy]-3H-benz(e)indol-3-yl}carbonyl]-1H-indol-5-yl]-5-[(3-methyldithio-1-oxopropyl)-amino]-1H-indole-2-carboxamide (DC2-SMe, 2b)

To a solution of (S)-N-[2-{(1-chloromethyl)-1,2-dihydro-5-hydroxy-3H-benz(e)indol-3-yl}carbonyl]-1H-indol-5-yl]-5-[(3-methyldithio-1-oxopropyl)-amino]-1H-indole-2-carboxamide (DC1SMe) DC1-SMe (1b, 40 mg, 0.058 mmol) in THF (4 mL) was added 4-nitrophenyl chloroformate (17 mg, 0.084 mmol) and di-isopropylethylamine (DIPEA, 15 µl). The reaction mixture was stirred under an Argon atmosphere for 3 h. Analysis by TLC showed all DC1 had been consumed to form an intermediate with an Rf value of 0.45 (mobile phase of 1:2 Acetone/Toluene). The reaction mixture was treated with 4-methylpiperazine (8.3 mg, 0.084 mmol), and then stirred overnight under Argon. The mixture was then diluted with a 1:1 (v/v))} mixture of EtOAc/THF (15 mL) and aqueous 1 M $NaH_2PO_4$, pH 5.0 (5 mL). The organic layer was separated, and the aqueous layer was extracted with EtOAc/THF (1:1, 4×15 ml). The organic layers were combined, dried over $MgSO_4$, filtered, evaporated, purified by silica gel chromatography, eluting with acetone/toluene, (3:8) and recrystallized with THF/EtOAc/Hexane to afford 40 mg (85% yield) of DC2-SMe (2b). Rf=0.31 (Acetone/Toluene, 3:8); mp=225° C. (dec.); $^1$H NMR (DMF-d7) 11.78 (s, 1H), 11.70 (s, 1H), 10.27 (s, 1H), 10.03 (s, 1H), 8.42 (d, 1H, J=1.7 Hz), 8.38 (s, 1H), 8.22 (d, 1H, J=1.7 Hz), 8.12 (d, 1H, J=8.4 Hz), 7.97 (d, 1H, J=8.2 Hz), 7.72 (dd, 1H, J=1.9, 8.8 Hz), 7.65 (dt, 1H, J=1.1, 7.0+7.0 Hz), 7.60 (d, 1H, J=8.9 Hz), 7.54 (t, 2H, J=7.4+8.6 Hz), 7.48 (d, 1H, J=1.4 Hz), 7.44 (dd, 1H, J=1.9, 8.8 Hz), 7.36 (d, 1H, J=1.6 Hz), 5.01 (t, 1H, J=10.0 Hz), 4.84 (dd, 1H, J=2.2, 10.9 Hz), 4.49 (m, 2H), 4.21 (dd, 1H, J=3.2, 11.3 Hz), 4.10 (m, 2H), 3.82 (m, 2H), 3.22 (m, 2H), 3.13 (t, 2H, J=7.0 Hz), 2.96 (m, 2H), 2.87 (t, 2H, J=7.1 Hz), 2.50 (s, 3H), 2.31 (s, 3H); $^{13}$C NMR 169.52, 161.13, 160.41, 153.73, 148.70, 142.72, 134.67, 134.49, 133.67, 133.36, 133.15, 132.16, 130.64, 128.41, 128.33, 128.22, 125.66, 125.59, 124.06, 123.10, 122.92, 119.97, 118.31, 113.49, 112.93, 112.90, 112.11, 111.66, 108.04, 106.98, 106.76, 103.80, 67.90, 67.65, 61.79, 55.82, 48.15, 42.68, 37.01, 34.56, 34.32, 23.36; MS m/z+ 831.14 (M+Na)$^+$, 833.13, 832.15, 847.14 (M+K)$^+$, 849.14, 848.14; MS m/z– 807.30 (M–H)–, 808.25, 809.26, 810.23.

Example II

Preparation of (S)-N-[2-{(1-chloromethyl)-1,2-dihydro-5-[(4-methylpiperazino)carbonyloxy]-3H-benz(e)indol-3-yl}carbonyl]-1H-indol-5-yl]-5-[(3-mercapto-1-oxopropyl)-amino]-1H-indole-2-carboxamide (DC2, 2a)

A solution of tris-(2-carboxyethyl) phosphine hydrochloride (TCEP, 30 mg, 0.104 mmol) in $H_2O$ (2 mL) was adjusted to pH 7.0 with $NaHCO_3$ powder. To the solution was added 25 mg (0.031 mmol) of DC2-SMe (2b) in DMA (3 mL). After stirring for 2 h, the pH was adjusted to between 3-4 by the addition of a few drops of HOAc. The mixture was concentrated and purified using preparative TLC on silica gel, eluting with acetone/toluene, 1:2) to yield 21 mg (90%) of DC2 (2a). $^1$H NMR (CD$_3$COCD$_3$) 10.91 (br, 2H), 10.81 (br, 1H), 9.56 (s, 1H), 9.19 (s, 1H), 8.37 (s, 1H), 8.38 (s, 1H), 8.15 (m, 1H), 8.02 (d, 1H, J=8.4 Hz), 7.94 (d, 1H, J=8.6 Hz), 7.63-7.55 (m, 3H), 7.47 (m, 1H), 7.36 (dd, 1H, J=2.1, 8.8 Hz), 7.29 (m, 1H), 7.21 (m, 1H), 5.44 (dd, 1H, J=2.0, 5.9 Hz), 4.85 (m, 2H), 4.40 (m, 2H), 4.10 (dd, 1H, J=3.2, 11.2 Hz), 3.92 (dd, 1H, J=7.8, 11.3 Hz), 3.81 (m, 2H), 3.22 (m, 2H), 3.08 (t, 2H, J=7.0 Hz), 2.87 (m, 2H), 2.82 (t, 2H, J=7.1 Hz), 2.38 (s, 3H); MS m/z+ 785.22 (M+Na), 786.20, 787.20, 801.14 (M+K), 803.16 (M+2+K); MS m/z– 762.10 (M–H), 764.05, 763.08.

Example III

Preparation of (S)-N-[2-{(1-chloromethyl)-1,2-dihydro-5-[(4-piperidino-piperidino)carbonyloxy]-3H-benz(e)indol-3-yl}carbonyl]-1H-indol-5-yl]-5-[(3-methydithio-1-oxopropyl)-amino]-1H-indole-2-carboxamide (DC3-SM2, 3b). (3b) (DC3-SMe)

To a solution of DC1-SMe, 1b, (50 mg, 0.073 mmol) in THF (4 ml) was added 4-nitrophenyl chloroformate (35 mg, 0.173 mmol) and DIPEA (50 µl). After stirring under Argon for 3 h, TLC analysis showed that all the DC1-SMe had been consumed to give an intermediate with Rf=0.45, 1:2 Acetone/Toluene). The reaction mixture was treated with 4-piperidino-piperidine (40 mg, 0.21 mmol), resulting in the formation of a heavy precipitate. The mixture was allowed to stir for 4 h, diluted with 20 ml of EtOAc/THF (1:1) and 5 ml of 1 M $NaH_2PO_4$, pH 4.5. The organic layer was separated, and the aqueous layer was extracted with EtOAc/THF (1:1, 4×15 ml). The organic layers were combined, dried over $MgSO_4$, filtered, evaporated, purified with Silica gel chromatography (Acetone/Toluene, 3:8) and crystallized with THF/EtOAc/Hexane to afford DC3-SMe (3b, 45 mg, 70% yield), mp=285° C. (dec.); [α]=29.7° (c 0.5 in DMF); $^1$H NMR 11.93 (s, 1H), 11.76 (s, 1H), 10.44 (s, 1H), 10.09 (s, 1H), 8.45 (s, 1H), 8.36 (s, 1H), 8.22 (s, 1H), 8.11 (d, 1H, J=8.3 Hz), 8.00 (d, 1H, J=8.4 Hz), 7.79 (dd, 1H, J=1.4, 8.6 Hz), 7.65 (t, 1H, J=7.5 Hz), 7.61-7.52 (m, 3H), 7.47-7.44 (m, 2H), 7.35 (d, 1H, j=1.0 Hz), 5.00 (t, 1H, J=10.0 Hz), 4.83 (dd, 1H, J=1.2, 10.2 Hz), 4.67 (m, 1H), 4.51 (m, 1H), 4.30 (m, 1H), 4.21 (dd, 1H, J=3.1, 11.1 Hz), 4.11 (m, 1H), 3.40 (m, 2H), 3.12 (t, 2H, J=7.0 Hz), 3.10 (m, 2H), 2.95 (m, 1H), 2.87 (t, 2H, J=7.1 Hz), 2.49 (s, 3H), 2.39 (m, 2H), 2.12 (m, 2H), 2.02-1.60 (m, 10H); $^{13}$C NMR 169.52, 162.90, 161.15, 160.34, 153.55, 148.47, 142.66, 134.66, 134.48, 133.76, 133.35, 133.29, 132.08, 130.63, 128.37, 128.22, 125.69, 125.52, 123.47, 123.11, 120.01, 118.01, 113.43, 112.89, 112.08, 111.72, 63.44, 60.08, 56.01, 50.00, 48.08, 42.62, 37.01, 34.07, 24.10, 24.08, 23.08, 22.78; MS m/z+ 878.24 (M+H)$^+$, 880.24, 879.25, 880.24; MS m/z– 876.40 (M–H)$^-$, 878.34, 877.37, 879.35.

Example IV

Preparation of (S)-N-[2-{(1-chloromethyl)-1,2-dihydro-5-[(4-piperidino-piperidino)carbonyloxy]-3H-benz(e)indol-3-yl}carbonyl]-1H-indol-5-yl]-5-[(3-mercapto-1-oxopropyl)-amino]-1H-indole-2-carboxamide (DC3, 3a). (3a) (DC3)

A solution of TCEP (15.2 mg, 0.053 mmol) in $H_2O$ (0.7 mL) was adjusted to pH 7.0 by the addition of 13.5 mg of $NaHCO_3$ powder. To the solution was added DC3-SMe (3b, 8.2 mg, 0.0093 mmol) in DMA (2 mL), and the reaction mixture was stirred for 2 h. A few drops of HOAc was then added to adjust the pH to between 3-4. The mixture was concentrated and purified using preparative TLC on silica gel, eluting with acetone/toluene, (1:2) to yield 7 mg of DC3 (3a). MS m/z+ 854.31 (M+Na)+, 855.31, 856.32, 857.31.

Example V

Preparation of (S)-N-[2-{(1-chloromethyl)-1,2-dihydro-5-(phosphonoxy)-3H-benz(e)indol-3-yl}carbonyl]-1H-indol-5-yl]-5-[(3-methyldithio-1-oxopropyl)-amino]-1H-indole-2-carboxamide (4b) (DC4-SMe)

A solution of DC1-SMe (1b, 50 mg, 0.073 mmol) in a mixture of THF (5 ml), $CH_3CN$ (4 ml) and DMA (0.5 ml) was stirred under an atmosphere of Argon. To the mixture were sequentially added $POCl_3$ (80 µL), DIPEA (150 µL) and DMAP (3 mg). After stirring for 2 h, both TLC and HPLC analyses showed that the DC1-SMe had been completely consumed. Aqueous 1.0 M $NaH_2PO_4$, pH 4.0 (2 ml) was added, and the mixture was stirred overnight. The mixture was further acidified with $H_3PO_4$ to pH 2.0, saturated with NaCl, and extracted with THF/EtOAc (1:1, 6×15 ml). The organic layer was separated, concentrated and the residue was recrystallized with THF/$H_2O$/$CH_3OH$ to afford 47 mg (84%) of the title compound (DC4-SMe).

$^1$H NMR (DMF-d7) 11.77 (s, 1H), 11.70 (s, 1H), 10.26 (s, 1H), 10.02 (s, 1H), 8.74 (s, 1H), 8.42 (s, 1H), 8.30 (d, 1H, J=7.6 Hz), 8.22 (s, 1H), 7.72 (d, 1H, J=8.3 Hz), 7.59 (m, 2H), 7.55-7.43 (m, 4H), 7.33 (s, 1H), 4.96 (t, 1H, J=9.8 Hz), 4.81 (d, 1H, J=10.2 Hz), 4.42 (m, 1H), 4.18 (m, 1H), 4.05 (dd, 1H, J=7.8, 11.0 Hz), 3.11 (t, 2H, J=7.0 Hz), 2.87 (t, 2H, J=7.1 Hz), 2.49 (s, 3H); $^{13}$C NMR 169.96, 161.45, 160.85, 143.10, 135.12, 134.93, 134.15, 133.81, 133.58, 132.80, 131.60, 128.86, 128.78, 128.02, 124.50, 124.05, 120.22, 118.61, 113.97, 113.40, 113.32, 112.57, 108.02, 104.27, 56.18, 48.60, 43.21, 37.47, 34.49, 23.53; $^{31}$P NMR −3.37; MS m/z 762.77 (M−H)$^−$, 764.80, 763.76.

Example VI

Preparation of (S)-N-[2-{(1-chloromethyl)-1,2-dihydro-5-(phosphonoxy)-3H-benz(e)indol-3-yl}carbonyl]-1H-indol-5-yl]-5-[(3-mercapto-1-oxopropyl)-amino]-1H-indole-2-carboxamide (4a) (DC4)

A solution of TCEP (30 mg, 0.104 mmol) in 2 ml of $H_2O$ was adjusted to pH 6.5-7.0 by the addition of $NaHCO_3$ powder. To the solution was added DC4-SMe (26 mg, 0.034 mmol) in 3 ml of DMA/$H_2O$ (1:1). After being stirred for 2 h under Argon, a few drops of 10% $H_3PO_4$ was added to reach pH 2.0. The mixture was then extracted with DMA/EtOAc (1:5, 6×10 ml). The organic layers were combined, evaporated and purified by preparative HPLC, using a C18 column, 20×250 mm, flow rate=8.0 ml/min., mobile phase: A: 0.01% HOAc in $H_2O$, B: 2% DMA in $CH_3CN$; time table: 0-10', 5% B; to 20', 20% B; to 50': 50% B. The DC4 peak eluted between 30-38 min. The fractions containing DC4 were pooled, concentrated and dried under vacuum to yield 22 mg (89%) of the title compound 4a. $^1$H NMR (DMF-d7) 11.76 (s, 1H), 11.69 (s, 1H), 10.26 (s, 1H), 10.02 (s, 1H), 8.78 (s, 1H), 8.41 (s, 1H), 8.29 (d, 1H, J=8.3 Hz), 8.21 (s, 1H), 7.79 (d, 1H, J=5.1 Hz), 7.60-7.43 (m, 6H), 7.27 (s, 1H), 4.96 (t, 1H, J=9.2 Hz), 4.80 (d, 1H, J=10.6 Hz), 4.42 (m, 1H), 4.23 (dd, 1H, J=2.2, 9.4 Hz), 4.06 (dd, 1H, J=7.4, 10.6 Hz), 3.12 (t, 2H, J=7.1 Hz), 2.88 (t, 2H, J=7.1 Hz); MS m/z 716.16 (M−H)$^−$, 717.12, 718.12.

Alternatively, to a solution of DTT (20 mg) in a mixture of acetone (3 mL) and 50 mM $NaH_2PO_4$ buffer (3 mL), pH 7.0 was added DC4SMe (22 mg, 0.028 mmol). After stirring under Argon for 4 h, a few drops of 5% $H_3PO_4$ was added to pH 3.0. The mixture was concentrated and purified on a C18 column (1.0'12 cm) eluted with 100% water to 50% water in acetone. The fractions were pooled and evaporated to dryness to afford 18 mg (90%) of DC4(4a). MS m/z− 716.30, 718.30, 717.30.

Example VII

Preparation of (S)-N-[2-{(1-chloromethyl)-1,2-dihydro-5-(dibenzylphosphonoxy)-3H-benz(e)indol-3-yl}carbonyl]-1H-indol-5-yl]-5-[(3-methyldithio-1-oxopropyl)-amino]-1H-indole-2-carboxamide (4c) (DC4-SMe dibenzylphosphate)

To a solution of DC1-SMe (50 mg, 0.073 mmol) in 10 ml of THF/$CH_3CN$ (1:1) under argon were sequentially added $CCl_4$ (100 µL, 1.036 mmol), DIPEA (55 µL, 0.316 mmol), dibenzylphosphite (100 µL, 0.452 mmol) and DMAP (0.2 mg, 0.0016 mmol). After stirring overnight under Argon, the reaction appeared complete by TLC analysis, with a new product being formed with an Rf=0.37 in acetone/toluene 1:2). The mixture was diluted with 5 ml of 1.0 M $NaH_2PO_4$, pH 4.0, and EtOAc (10 mL). The organic layer was separated and the aqueous solution was extracted with THF/EtOAc (1:1, 4×15 ml). The organic layers were combined, dried over MgSO4, filtered, evaporated and purified by silica gel chromatography, eluting with acetone/toluene (3:7), to afford 62 mg (89%) of the title compound 4c. $^1$H NMR (DMF-d7) 11.84 (s, 1H), 11.74 (s, 1H), 10.31 (s, 1H), 10.04 (s, 1H), 8.77 (s, 1H), 8.44 (s, 1H), 8.22 (s, 1H), 8.10 (t, 2H, J=7.3 Hz), 7.74 (dd, 1H, J=1.7, 8.8 Hz), 7.66-7.61 (m, 2H), 7.55-7.29 (m, 15H), 5.37 (t, 4H, J=7.5 Hz), 5.01 (m, 2H), 4.84 (dd, 1H, J=1.9, 10.9 Hz), 4.51 (m, 1H), 4.20 (dd, 1H, J=3.2, 10.9 Hz), 4.11 (dd, 1H, J=6.9, 11.1 Hz), 3.13 (t, 2H, J=7.2 Hz), 2.87 (t, 2H, J=7.1 Hz), 2.50 (s, 3H); $^{13}$C NMR 169.52, 161.18, 160.41, 147.88, 147.20, 136.74, 136.67, 134.68, 134.56, 133.70, 133.36, 133.20, 132.11, 130.83, 129.25, 129.23, 129.21, 129.19, 128.84, 128.78, 128.62, 128.42, 128.32, 127.90, 124.28, 124.22, 123.96, 123.33, 122.87, 120.03, 118.32, 113.51, 112.94, 112.12, 108.42, 106.87, 70.75, 70.69,, 67.91, 55.90, 47.96, 42.59, 37.02, 34.04, 23.08; $^{31}$P NMR −4.49; MS m/z 966.17 (M+Na)$^+$, 968.14 (M+2+Na), 967.17.

Conversion to DC4:

A flask was charged with 4c (20 mg, 0.021 mmol), and treated with Pd/C (15 mg), glacial acetic acid (100 µl) and DMA (4 ml). The system was evacuated with vacuum suction, and then stirred under hydrogen through a hydrogen-filled balloon overnight. The catalyst was removed by filtration and the solvent was evaporated, and the residue was purified by preparative HPLC as above described to yield 6 mg (39%) of DC4 (4a). MS m/z 716.48 (M−H)$^−$, 717.48, 718.50.

Example VIII

Preparation of (S)-N-[2-{(1-chloromethyl)-1,2-dihydro-5-hydroxy-3H-benz(e)indol-3-yl}carbonyl]-1H-indol-5-yl]-5-nitro-1H-indole-2-carboxamide (DC0, 10a)

To a solution of 5-hydroxy-3-amino-1-[S]-(chloromethyl)-1,2-dihydro-3H-benz(e)indole, hydrochloride salt [seco-(−) CBI, 20 mg, 0.72 mmol] and 5-[5'-nitroindol-2'-yl-carbonyl amino]indole-2-carboxylic acid (9, 25 mg, 0.068 mmol) in DMA (3 mL) was added EDC (40 mg, 0.20 mmol) under Argon. After stirring overnight, a few drops of 50% HOAc were added and the mixture was evaporated to dryness and purified by preparative silica gel TLC chromatography (40% acetone in toluene) to afford 25 mg of DC0 (10a). $^1$H NMR (DMF-d$_7$) 12.54 (s, 1H), 11.73 (s, 1H), 10.60 (s, 1H), 10.58 (s, 1H), 8.80 (d, 1H, J=2.3 Hz), 8.42 (d, 1H, j=1.9 Hz), 8.25 (d, 1H, J=8.5 Hz), 8.19 (dd, 1H, J=2.1, 9.1 Hz), 8.09 (br, 1H), 7.95 (d, 1H, J=8.3 Hz), 7.82 (d, 1H, J=1.5 Hz), 7.79 (d, 1H, J=9.1 Hz), 7.74 (dd, 1H, J=2.0, 8.9 Hz), 7.62 (d, 1H, J=8.8 Hz), 7.58 (dt, 1H, J=1.7, 7.0+7.0 Hz), 7.42 (dt, 1H, J=1.2, 7.0+7.0 Hz), 7.33 (d, 1H, J=1.7 Hz), 4.91 (t, 1H, J=11.0 Hz), 4.77 (dd, 1H, J=2.1, 11.1 Hz), 4.33 (m, 1H), 4.13 (dd, 1H, J=3.1, 11.1 Hz), 3.97 (dd, 1H, J=7.9, 11.1 Hz); $^{13}$C NMR 163.35, 161.48, 160.05, 155.79, 142.98, 137.18, 135.03, 133.22, 133.16, 131.50, 128.85, 128.45, 128.11, 124.62, 124.02, 123.76, 120.33, 119.36, 118.70, 116.45, 114.00, 113.08, 106.97, 105.02, 101.53; MS m/z 602.96 (M+Na)$^+$, 604.78, 603.81, 618.64 (M+K)$^+$, 620.48.

Example IX

Preparation of (S)-N-[2-{(1-chloromethyl)-1,2-dihydro-5-hydroxy-3H-benz(e)indol-3-yl}carbonyl]-1H-indol-5-yl]-5-[(3-methyldithio-1-oxopropyl)-amino]-1H-indole-2-carboxamide, DC1SMe (1b)

A flask was charged with 10a (10 mg, 0.017 mmol), Pd/C (10 mg), HCl (conc. 3 μl) and DMA (2.5 ml). After the air was evacuated, hydrogen was conducted by hydrogen balloon overnight. The catalyst was removed by filtration and the solvent was evaporated to give 10b as a brown solid. The solid compound was used directly without further purification.

To 10b in DMA (2 mL) was added 3-(methyldithio)propionic acid (5 mg, 0.032 mmol) and EDC (15 mg, 0.078 mmol) under Argon. After stirring overnight, two drops of 50% HOAc were added, and the mixture was evaporated to dryness and purified by preparative silica gel TLC (40% acetone in toluene) to afford 6 mg of DC1-SMe (1b) R$_f$=0.40 (3:7 Acetone/Toluene); $^1$H NMR (CD$_3$COCD$_3$) 10.91 (s, 1H), 10.88 (s, 1H), 9.64 (s, 1H), 9.56 (s, 1H), 9.27 (s, 1H), 8.35 (d, 1H, J=1.9 Hz), 8.25 (d, 1H, J=8.0 Hz), 8.17 (d, 1H, J=1.9 Hz), 8.07 (s, 1H), 7.88 (d, 1H, J=8.3 Hz), 7.64 (dd, 1H, J=2.0, 8.1 Hz), 7.58-7.50 (m, 3H), 7.38-7.35 (m, 2H), 7.31 (d, 1H, J=1.7 Hz), 7.26 (d, 1H, J=1.7 Hz), 4.86 (dd, 1H, J=8.7, 11.0 Hz), 4.80 (dd, 1H, J=2.3, 10.9 Hz), 4.30 (m, 1H), 4.07 (dd, 1H, J=3.1, 11.0 Hz), 3.83 (dd, 1H, J=8.4, 11.2 Hz), 3.09 (t, 2H, J=7.1 Hz), 2.83 (t, 2H, J=7.1 Hz), 2.45 (s, 3H); $^{13}$C NMR 169.56, 161.10, 160.43, 155.13, 143.50, 134.78, 134.46, 133.55, 133.34, 133.03, 132.57, 131.21, 128.80, 128.69, 128.21, 124.22, 124.02, 123.53, 123.44, 120.16, 118.79, 116.45, 113.91113.02, 112.95, 112.73, 106.78, 103.72, 101.63, 56.01, 47.73, 43.10, 37.25, 34.01, 23.00; MS m/z 706.71 (M+Na)$^+$, 708.58, 707.71, 722.34 (M+K)$^+$, 724.42.

Example X

Preparation of (S)-N-[2-{(1-chloromethyl)-1,2-dihydro-5-hydroxy-3H-benz(e)indol-3-yl}carbonyl]-1H-indol-5-yl]-5-[(15"-methyldithio-4",7",10",13"-tetraoxapentadecyl-1-oxopropyl)-amino]-1H-indole-2-carboxamide (DC5-SMe)

To a solution of 10b (50 mg, 0.091 mmol) in DMA (5 mL) was added 15"-methyldithio-4",7",10",13"-tetraoxapentadecanoic acid (33 mg 0.100 mmol) and EDC (88 mg, 0.459 mmol) under Ar. After being stirred overnight, two drops of 50% HOAc were added to the mixture and the mixture was evaporated to dryness, purified by Silica gel chromatography (30% acetone in toluene) to afford DC5-SMe Certain patents and printed publications have been referred to in the present disclosure, the teachings of which are hereby each incorporated in their respective entireties by reference.

While the invention has been described in detail and with reference to specific embodiments thereof, it will be apparent to one of skill in the art that various changes and modifications can be made thereto without departing from the spirit and scope thereof.

What is claimed is:

1. A prodrug of an analog of CC-1065 having two subunits linked by an amide bond, wherein the first subunit is a seco-CBI (cyclopropabenziindole) molecule represented by the following formula:

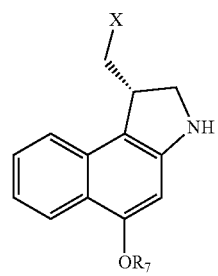

wherein X is halogen, and wherein the second subunit is a monoindolyl moiety of formula:

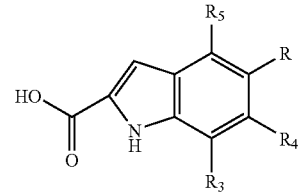

wherein R represents a moiety that enables linkage of said prodrug to a cell binding agent; $R_3$, $R_4$, and $R_5$ are each independently hydrogen, C1-C3 linear alkyl, methoxy, hydroxyl, primary amino, secondary amino, tertiary amino, or amido; and $R_7$ is piperazino carbamate, 4 piperidino-piperidino carbamate or phosphate.

2. The prodrug of claim 1, wherein R comprises a thiol or a disulfide bond.

3. The prodrug of claim 1, wherein R is selected from the group consisting of NHCO(CH$_2$)$_m$SZ, NHCOC$_6$H$_4$(CH$_2$)$_m$ SZ, NHCOC$_6$H$_4$O(CH$_2$)$_m$SZ, NHCO(CH$_2$)$_m$(OCH$_2$CH$_2$)$_n$ SZ, NHCOC$_6$H$_4$(CH$_2$)$_m$(OCH$_2$CH$_2$)$_n$SZ, and NHCOC$_6$H$_4$O (CH$_2$)$_m$(OCH$_2$CH$_2$)$_n$SZ wherein: Z represents H or SR$_8$, wherein R$_8$ represents methyl, linear alkyl, branched alkyl, cyclic alkyl, simple or substituted aryl or heterocyclic selected from the group consisting of furyl, pyrrollyl, pyridyl, and thiophene, m represents an integer of 1 to 10, and n represents an integer of 4 to 1000.

4. The prodrug of claim 1, wherein R is selected from the group consisting of NHCO(CH$_2$)$_m$(OCH$_2$CH$_2$)$_n$SZ, NHCOC$_6$H$_4$(CH$_2$)$_m$(OCH$_2$CH$_2$)$_n$SZ, and NHCOC$_6$H$_4$O (CH$_2$)$_m$(OCH$_2$CH$_2$)$_n$SZ wherein: Z represents H or SR$_8$, wherein R$_8$ represents methyl, linear alkyl, branched alkyl, cyclic alkyl, simple or substituted aryl or heterocyclic selected from the group consisting of furyl, pyrrollyl, pyridyl, and thiophene, m represents an integer of 1 to 10, and n represents an integer from 2 to 1000.

5. The prodrug of claim 1, wherein R is selected from the group consisting of $NHCO(CH_2)_2SH$, $NHCO(CH_2)_2SSCH_3$, $NHCO(CH_2)_2(OCH_2CH_2)_nSH$ and $NHCO(CH_2)_2(OCH_2CH_2)_nSSCH_3$.

6. The prodrug of claim 1, wherein R is $NHCO(CH_2)_2SSCH_3$.

7. A method for treating a subject by inhibiting the growth of cells of or by killing cells of a selected cell population, comprising administering to a subject in need of treatment an effective amount of the prodrug of any one of claim 1, 3, 4, 5 and 6.

* * * * *

UNITED STATES PATENT AND TRADEMARK OFFICE
CERTIFICATE OF CORRECTION

PATENT NO. : 7,655,660 B2  
APPLICATION NO. : 11/649822  
DATED : February 2, 2010  
INVENTOR(S) : Robert Yongxin Zhao and Ravi V. J. Chari It is certified that error appears in the above-identified patent and that said Letters Patent is hereby corrected as shown below:

In claim 1 at column 20, lines 49-50:

delete "$R_7$ is piperazine carbamate, 4-piperidino-piperidino carbamate or phosphate" and insert -- $R_7$ is phosphate or together with the adjacent O atom in the formula forms a piperazine carbamate, or a 4-piperidino-piperidino carbamate --

Signed and Sealed this

Fifteenth Day of June, 2010

David J. Kappos  
*Director of the United States Patent and Trademark Office*